United States Patent
Bentley et al.

(10) Patent No.: US 7,456,207 B2
(45) Date of Patent: Nov. 25, 2008

(54) VAGINAL PHARMACEUTICAL COMPOSITIONS AND METHODS FOR PREPARING THEM

(75) Inventors: Christine Lynn Bentley, Caledonia, MI (US); Karen Feldtmose, Pennsburg, PA (US)

(73) Assignee: Teva Pharmaceuticals USA, Inc. PA (US)

( * ) Notice: Subject to any disclaimer, the term of this patent is extended or adjusted under 35 U.S.C. 154(b) by 0 days.

(21) Appl. No.: 10/946,133

(22) Filed: Sep. 22, 2004

(65) Prior Publication Data

US 2005/0080038 A1 Apr. 14, 2005

Related U.S. Application Data

(60) Provisional application No. 60/505,448, filed on Sep. 25, 2003.

(51) Int. Cl.
*A01N 43/50* (2006.01)
*A61F 6/06* (2006.01)

(52) U.S. Cl. .................. 514/396; 514/398; 424/430

(58) Field of Classification Search ................ 514/396, 514/398; 424/430
See application file for complete search history.

(56) References Cited

U.S. PATENT DOCUMENTS

| 4,837,378 | A |   | 6/1989  | Borgman |
|-----------|---|---|---------|---------|
| 5,536,743 | A | * | 7/1996  | Borgman ............... 514/398 |
| 5,536,744 | A |   | 7/1996  | Okumura et al. |
| 5,840,744 | A | * | 11/1998 | Borgman ............... 514/398 |
| 6,348,203 | B1| * | 2/2002  | Goodman et al. ........ 424/401 |
| 2003/0064103 | A1 | * | 4/2003 | Lin et al. ................ 424/486 |
| 2003/0119783 | A1 | * | 6/2003 | Chang et al. ............ 514/58 |

FOREIGN PATENT DOCUMENTS

| EP | 747045 A2 | * | 12/1996 |
| GB | 2199495 A | * | 7/1988 |
| RO | 80363 |   | 2/1983 |

* cited by examiner

*Primary Examiner*—Sreeni Padmanabhan
*Assistant Examiner*—Renee Claytor
(74) *Attorney, Agent, or Firm*—Kenyon & Kenyon LLP

(57) ABSTRACT

Vaginal pharmaceutical compositions are described. These compositions contain (i) an active pharmaceutical ingredient selected from the group consisting of antimicrobial imidazoles and mixtures thereof, and (ii) a polysaccharide, wherein the pH of the composition is greater than 4.25 and less than about 8. In particularly preferred compositions, the active pharmaceutical ingredient includes metronidazole and the polysaccharide includes hypromellose. These compositions can be applied to vaginal tissue for treatment of various diseases, such as bacterial vaginosis, or for prophylaxis.

2 Claims, No Drawings

VAGINAL PHARMACEUTICAL COMPOSITIONS AND METHODS FOR PREPARING THEM

CROSS-REFERENCE RELATED APPLICATION

This application claims priority under 35 USC §119(e) to provisional application Ser. No. 60/505,448, filed Sep. 25, 2003, which is incorporated herein in its entirety.

FIELD OF THE INVENTION

The invention relates to vaginal pharmaceutical compositions containing an antimicrobial imidazole, such as metronidazole, that can be used, for example, in treating bacterial vaginosis.

BACKGROUND

Normal vaginal flora is reported to be composed predominantly of *Lactobacillus* species, with an average pH of about 4.0. This low pH is reported to foster growth and maintenance of the acidophilic *Lactobacilli* that dominate the normal flora.

Metronidazole is an antibacterial compound that has been used to treat various microbial diseases, including bacterial vaginosis (BV). Metronidazole has been reported to be effective in treating BV when administered orally. For example, as of 1985, the Center for Disease Control recommended an oral dose of 500 mg of metronidazole twice daily for seven days.

MetroGel-Vaginal® (3M, St. Paul, Minn.) is a product containing 0.75% metronidazole, methylparaben, propylparaben, edetate disodium, Carbomer 934P, propylene glycol, water, and sodium hydroxide to pH 4.0. The Food and Drug Administration's Approved Drug Products and Therapeutic Equivalents (The "Orange Book") lists, for MetroGel-Vaginal®, U.S. Pat. No. 5,536,743 ("the '743 patent"), Pat. No. 5,536,744 ("the '744 patent"), and Pat. No. 4,837,378 ("the '378 patent").

The '743 and the '744 patents describe compositions and methods directed to the treatment of bacterial vaginosis. These patents describe metronidazole in a buffered, non-flowing pharmaceutical composition having a pH value below 4.25. These patents repeatedly emphasize the criticality of the low pH of the composition. For instance, in Example 12 in each of these two patents, the clinical cure rate of MetroGel-Vaginal® (pH 4) was found to be superior to the same composition at pH 6. The conclusion was that these results "underscore clearly the advantage of the relatively lower pH value for the vaginal preparation."

The '378 patent is directed to aqueous metronidazole gels containing water-dispersible polycarboxylated vinyl polymers (such as Carbopol® (Noveon Pharmaceuticals, Cleveland, Ohio)) for the treatment of skin disorders.

U.S. Pat. No. 6,348,203 ("the '203 patent") is directed toward imidazole derivatives that can be used in the topical treatment of certain dermatological diseases. The '203 patent discloses compositions that are specially formulated and buffered to a pH that is within the physiologically tolerable range for dry or inflamed skin. The '203 patent, however, does not teach or suggest whether the disclosed compositions could be suitable for applying to vaginal tissue for treatment or prevention of vaginal diseases, let alone the appropriate dosage for vaginal treatment.

Romanian Patent No. 80,363, published Nov. 30, 1982, describes a vaginal gel containing antifungal, antiparasitic, and large amounts of antibacterial agents (such as metronidazole) in a Carbopol® 940 base.

Flagyl® (G.D. Searle & Co., Skokie, Ill.) is a pharmaceutical product that has been approved in Canada. In one form, it is a high-dose (500 mg) vaginal cream containing 10% metronidazole, glycerin, glyceryl monostearate, methylparaben, propylparaben, purified water, stearic acid, and triethanolamine for the treatment of trichomoniasis.

SUMMARY OF THE INVENTION

One embodiment of the invention is a vaginal pharmaceutical composition comprising (i) an active pharmaceutical ingredient selected from the group consisting of antimicrobial imidazoles and mixtures thereof, and (ii) a polysaccharide, wherein the pH of the composition is greater than 4.25 and less than about 8. In particularly preferred embodiments of the invention, the active pharmaceutical ingredient comprises metronidazole, the polysaccharide comprises hypromellose, or both. Another embodiment of the invention is a method for preparing a composition of the invention. The composition of the invention can be applied to vaginal tissue for treatment of certain diseases or for prophylaxis.

Unless otherwise indicated, all percentages refer to percent by weight of the composition.

DETAILED DESCRIPTION OF THE INVENTION

The inventors have unexpectedly discovered that certain compositions containing an antimicrobial imidazole, such as metronidazole, and a polysaccharide are highly effective in treating microbes in low doses and at a pH of greater than 4.25.

A preferred embodiment of the invention is a viscous vaginal pharmaceutical composition comprising an active pharmaceutical ingredient selected from the group consisting of antimicrobial imidazoles and mixtures thereof, and a polysaccharide, wherein the pH of the composition is greater than 4.25 and less than about 8. Advantageously, the composition does not require a buffering system.

The active pharmaceutical ingredient (API) of the composition is one or more antimicrobial imidazoles. Examples of suitable imidazoles include metronidazole, terconazole, clotrimazole, econazole, ketoconozole, miconazole, sulconazole, tioconazole, and the like. As used herein, "antimicrobial" refers to an agent that suppresses or kills bacteria, protozoa, or other microbes.

One of ordinary skill in the art would appreciate that the preferred amount of API in a given composition depends on the particular antimicrobial agent(s) used and other factors, such as the particular carrier used. For metronidazole, the preferred amount is about 0.1 to about 2 wt %, preferably about 0.5 to about 1 wt %, more preferably about 0.75 wt %. Preferred amounts of other imidazoles are as follows:

| | |
|---|---|
| terconazole | about 0.4% to about 0.8% |
| clotrimazole | about 1% to about 10% |
| econazole | about 1% |
| ketoconazole | about 2% |
| miconazole | about 2% to about 4% |
| sulconazole | about 1% |
| tioconazole | about 6.5% |

Likewise, the preferred quantity of API contained in a unit dose also depends on the particular antimicrobial agent(s) used and other factors, such as the particular carrier used. For metronidazole, the unit dose is generally at least about 20 mg, and is generally not more than about 375 mg. A preferred unit dose of metronidazole in a gel vehicle is in the range of about 20 to about 40 mg, more preferably about 37.5 mg. Preferred amounts of other imidazoles are as follows:

| | |
|---|---|
| terconazole | about 20 mg to about 140 mg |
| clotrimazole | about 100 mg to about 600 mg |
| ketoconazole | about 200 mg to about 400 mg |
| miconazole | about 100 mg to about 1200 mg |
| tioconazole | about 300 mg to about 1200 mg |

A unit dose can be administered one to three times daily (that is, at spaced intervals in a 24 hour period) for up to ten days. Thus, the total daily dose of metronidazole delivered can range from about 20 to about 375 mg, preferably about 20 to about 100 mg, more preferably about 20 to about 40 mg. In a gel form of a metronidazole composition, a daily dose in the range of about 30 to about 40 mg usually is sufficient. The total dose during the course of therapy for metronidazole compositions of the present invention is preferably in the range of about 100 mg to about 375 mg. The total dose of other APIs can be similarly calculated.

In a preferred embodiment, about 5 g of a gel containing 0.75% metronidazole is administered once or twice daily for a period of about five days, thereby delivering a total dose of about 185 mg to about 375 mg. Such doses are significantly lower than that described previously for oral administration of metronidazole. Lower doses decreases the risk of dose-related side effects.

For prophylactic purposes, the amount of metronidazole administered is preferably in the range of about 20 mg to about 80 mg, more preferably in the range of about 30 to about 40 mg per dose. For other APIs, the dosage can be adjusted downward in a like manner. These prophylactic amounts can be introduced intravaginally as a single dose or more than one dose, as desired, preferably twice a week on non-consecutive days.

The term "unit dose" as used in the specification and claims refers to a physically discrete amount of a pharmaceutical composition that is suitable for itemized administration to a patient. Over the course of treatment, a patient may receive one or more unit doses. The preferred unit dose will also depend on other factors well known by those of skill in the art, including, for example, the nature and severity of the disease, the weight, age, and health of the patient, etc.

In a preferred embodiment of the invention, the composition is sufficiently viscous that the composition stays adhered to the target tissue for a sufficient time to deliver an adequate amount of the API. The preferred viscosity will depend on factors such as the rate of penetration of the API, the quantity of the composition that is applied, whether the patient upright or lying down (for example, bedtime applications), etc.

The composition, which contains a polysaccharide, may be in the form of a gel, paste, cream, ointment, and the like. A gel is most preferred.

To achieve the desired viscosity, a sufficient amount of one or more polysaccharides may be used. Typically, about 0.25 to about 10 wt % polysaccharide (based on the total weight of the composition) is desirable, more preferably about 2.5 to about 7 wt %.

To increase the viscosity of the composition, the polysaccharide may be used in conjunction with one or more non-polysaccharide viscosifiers known in the art. In the absence of a non-polysaccharide viscosifier, the polysaccharide is preferably about 3 to about 4.5 wt %, more preferably about 3.5 wt %.

The polysaccharide of the invention is preferably a cellulose derivative, preferably a non-ionic cellulose ester, ether, hydroxy-ether, or hydroxy-ester, or a non-ionic starch derivative. The polysaccharide can be, for example, a methyl, ethyl, or propyl cellulose ester, ether, hydroxy-ether, or hydroxy-ester. Preferably, the polysaccharide is a hydroxyalkyl cellulose, more preferably hypromellose (also known as hydroxypropyl methylcellulose).

In a preferred embodiment, it is desirable to have a highly viscous composition without exceeding 3.5 wt % polysaccharide. For such an embodiment, it is therefore preferred to use a relatively high-viscosity polysaccharide, such as Methocel E10M, which has an apparent viscosity of 4646-7070 mPa by rotation and 7500-14,000 cP by Ubbelhode.

Examples of possible non-polysaccharide viscosifiers that could be used in conjunction with one or more polysaccharides include xantham gum, alginic acids and salts thereof, magnesium aluminum silicate, dextrins, sucrose and derivatives thereof, and mixtures thereof. The amount of non-polysaccharide viscosifier, if present, is about 0.1 to about 10 wt %.

In a preferred embodiment, the viscosity of the composition is substantially unaffected by changes in pH.

Preferred embodiments of the invention contain one or more pharmaceutically acceptable preservatives. As used herein, the term "preservative" includes an agent or a combination of agents that aids in stabilizing the composition, inhibiting microbe growth, or both. Examples of suitable preservatives include parabens (e.g., methyl, ethyl, propyl, and butyl esters of parahydroxybenzoic acid), propyl gallate, sorbic acid and its sodium and potassium salts, propionic acid and its calcium and sodium salts, "Dioxin" (6-acetoxy-2,4-dimethyl-m-dioxane), "Bronopol" (2-bromo-2-nitropropane-1,3-diol) and salicylanilides such as disbromosalicylanilide, tribromosalicylamilides, "Cinaryl" 100 and 200 or "Dowicil" 100 and 200 (Cis isomer of 1-(3-chloroallyl-3,5,7-triaza-1-azanidadamantane chloride), hexachlorophene, sodium benzoate, citric acid, ethylene diaminetetraacetic acid and its alkali metal and alkaline earth metal salts, butyl hydroxyanisol, butyl hydroxytoluene, phenolic compounds such as chloro- and bromocresols and chloro- and bromo-oxylenols, quaternary ammonium compounds like benzalkonium chloride, aromatic alcohols such as phenylethyl alcohol, benzyl alcohol, etc., chlorobutanol, quinoline derivatives such as iodochlorohydroxyquinolin, and the like. Additional examples of pharmaceutically acceptable preservatives can be found, for example, in *Handbook of Pharmaceutical Additives* (Synapse Information Resources, Inc.), which is incorporated herein by reference. A particularly preferred preservative system is a combination of methylparaben and propylparaben.

The total amount of preservative, when present, is preferably about 0.005 to about 2 wt %, more preferably about 0.1 wt %.

In a preferred embodiment of the invention, the pharmaceutical composition is water-based and contains a cosolvent. For the cosolvent, monohydric alcohols can be used, such as those having from 1 to 22 carbons per molecule, such as methanol, ethanol, propanol, isopropanol, butanol, hexanol, cetyl alcohol, stearyl alcohol, and the like. Dihydric and polyhydric alcohols can be used, such as those having from 2 to 22 carbons per molecule, such as propylene glycol, glycerin, hexanetriols, such as 1,2,6-hexanetriol, sorbitol, 1,3-butanediol, 2,3-butanediol, and the like. Polyethylene glycols and polypropylene glycols can be used, such as those having molecular weight in the range of about 100 to about 20,000. Esters of aliphatic monobasic and dibasic acids can be used, such as those having from 2 to 22 carbons per molecule, with (a) monohydric alcohols having from 1 to 20 carbons per molecule, (b) di- and polyhydric alcohols having from 2 to 20 carbons per molecule, and (c) sugar alcohols. Examples include isopropyl myristate, myristyl myristate, cetyl stearate, methyl stearate, isopropyl sebacate, methyl sebacate, sucrose monolaurate, sucrose monostearate, and the like. Propylene glycol, a polyethylene glycol, hexylene glycol, oleic acid, a polyoxyethylene, glycerin, or mixtures thereof are preferred. Propylene glycol is most preferred.

The preferred amount of cosolvent, when present, is about 0.5 to about 40 wt %, preferably about 3 wt %.

In a preferred embodiment of the invention, the pharmaceutical composition contains a chelating agent, such as those known to those skilled in the art. Preferably, the chelating agent is EDTA or a salt thereof. The composition preferably contains about 0.003 to about 1 wt % chelating agent, preferably about 0.02 to about 0.2 wt %, more preferably about 0.05 wt %.

The pH of the composition of the invention is not critical, but preferably ranges from 4.25 to about 8, more preferably from about 5 to about 6.5.

According to an embodiment of the invention, there is provided a viscous vaginal pharmaceutical composition comprising an aqueous gel of: about 0.75% metronidazole; about 3.5% hypromellose; about 3% propylene glycol; about 0.05% edetate disodium; about 0.08% methylparaben; about 0.02% propylparaben; and about 93% water, wherein the pH of the composition is from about 5 to about 6.

Another embodiment of the invention is a method for preparing a pharmaceutical composition according to the invention. Water is admixed with an antimicrobial imidazole, a polysaccharide, optionally, a chelating agent, optionally, a water-miscible cosolvent, and optionally, a preservative. Preferably, the composition that is formed is a gel. Optionally, the pH can be adjusted.

Preferably, the composition is prepared by, first, admixing a polysaccharide and water to form a first mixture. Second, an imidazole and, optionally, a cosolvent is dissolved in the first mixture to form a second mixture. Preferably, the second mixture is cooled to about room temperature prior to storage.

The temperature of the various components is not critical, but preheating the water to about 25° C. to about 90° C. expedites thorough mixing. Preheating the water to about 70° C. to about 80° C. has been found to be a particularly convenient temperature.

Another embodiment of the invention is a method for treating vaginal tissue comprising applying the composition of the invention to targeted vaginal tissue. As used herein, "vaginal tissue" includes the vagina, cervix, and vulva. For most applications, it is envisioned that the vagina will be the principal vaginal tissue that will be targeted. The composition of the invention may be applied to vaginal tissue either to treat diseased tissue or prophylactically.

In one embodiment, the composition of the invention is dispensed from an applicator that is inserted into the vagina and removed. Alternatively, the composition can be put into a vaginal insert, for example, that remains in the vagina as a means of controlling the dose. A vaginal insert of this type might be porous, have holes, or have other mechanisms known in the art to control dosing.

The practice of the present invention is demonstrated in the following examples. These examples are meant to illustrate the invention rather than to limit its scope.

EXAMPLES

Example 1

Preparation of Metronidazole Gel USP, 0.75% Vaginal

TABLE I

Formulation

| Ingredient | Quantity (g) |
|---|---|
| Metronidazole, USP | 0.75 |
| Propylene Glycol, USP | 3.00 |
| Edetate Disodium, USP | 0.05 |
| Methylparaben, NF | 0.08 |
| Propylparaben, NF | 0.02 |
| Hydroxypropylmethylcellulose (Methocel E10M Premium) | 3.50 |
| Purified Water, USP | 92.6 |
| TOTAL (theoretical weight) | 100 |

551.6 kg purified water, USP, was transferred to a 1000 L stainless steel jacketed tank equipped with dual counter-rotating blades with side-scrapers and a high-shear mixer. While mixing (blades/side scrapers about 12 RPM, high-shear mixer on high), the water was heated to 75° C. and maintained at that temperature. After reaching 75° C., 0.480 kg methylparaben, NF, was added and mixing continued until the methylparaben was dissolved. While mixing, 0.120 kg propylparaben, NF, was added and mixing continued until it was completely dissolved. While mixing, 0.300 kg edetate disodium, USP, was added and mixing continued until it was completely dissolved. While mixing, 21.000 kg hydroxypropyl methylcellulose 2910 (Methocel E10M) was added to the tank and mixing continued until it was completely dispersed. While mixing, 18.00 kg propylene glycol, USP, was added and mixing continued until it was completely dissolved. While mixing, 4.500 kg metronidazole, USP, was added and mixing continued until it was completely dissolved. The pH was measured to be about 5.2 (bottom) to about 5.9 (top). While mixing, 4.000 kg purified water, USP, was added and mixed for 15 minutes. The high shear mixer was turned off and the mixture was cooled to about 24° C. over about 4.5 h. The resulting gel was then stored in a 500 gallon tank, followed by packaging in 70 g tubes. Samples from various tubes throughout the batch were found to have a pH of about 5.3.

Example 2

Clinical Trial Comparison to MetroGel-Vaginal®

A multi-center, double-blind, randomized parallel-group clinical study was conducted to investigate the efficacy, safety, and tolerability of Example 1 of the invention for the treatment of BV. The study was conducted according to Good Clinical Practice (GCP) regulations and U.S. Food and Drug Administration (FDA) regulations (CFR 21 Parts 50, 54, 56, and 312).

Below is a comparison of the ingredients of the vaginal gel of Example 1 ("test") and MetroGel-Vaginal® ("reference"):

| Metronidazole Vaginal Gel (Example 1) | MetroGel-Vaginal ® (reference) |
|---|---|
| Metronidazole, USP (0.75%) | Metronidazole (0.75%) |
| Methylparaben, NF | Methylparaben |
| Propylparaben, NF | Propylparaben |
| Edetate Disodium, USP | Edetate Disodium |
| Methocel (E10M Premium) | Carbomer (934P) |
| Propylene Glycol, USP | Propylene Glycol |
|  | Sodium Hydroxide to pH to 4.0 |
| Purified Water, USP | Purified Water |

The inclusion criteria for the study were the following:
1. Consent
2. Clinical diagnosis of BV, defined as having the presence of "clue cells"≧20% of the total epithelial cells on microscopic examination of a saline "wet mount" and all of the following criteria:
   Off-white (milky or gray), thin, homogeneous discharge
   pH of vaginal fluid≧4.7
   A positive 10% KOH "whiff test" (a fishy amine odor upon the addition of a 10% KOH solution to a vaginal discharge sample)
3. Subjects were 18 years of age or older with no known medical conditions that, in the investigator's opinion, might interfere with study participation.
4. Women of childbearing potential had a negative urine pregnancy test result upon entry into the study.
5. Subjects agreed to abstain from sexual intercourse throughout the first seven days of the study. Following the first 7 days, the subjects agreed to use a non-lubricated condom when engaging in sexual intercourse.
6. Subjects agreed to abstain from alcohol ingestion during the five-day treatment period and for one day afterward.
7. Subjects agreed to refrain from the use of intra-vaginal products throughout the study (e.g., douches, feminine deodorant sprays, spermicides, lubricated condoms, tampons, and diaphragms).

The exclusion criteria were the following:
1. Subjects with known or suspected other infectious causes of vulvovaginitis (e.g., candidiasis, *Trichomonas vaginalis, Chlamydia trachomatis, Neisseria gonorrhoeae*, active *Herpes simplex*, or human papilloma virus, or any other vaginal or vulvar condition, which in the investigator's opinion, would confound the interpretation of clinical response).
2. Subjects with a Gram's stain slide Nugent score<4.
3. Subjects who received antifungal or antimicrobial therapy (systemic or intravaginal) within 14 days of randomization.
4. Subjects who had taken disulfuram within 14 days of randomization.
5. Subjects who have demonstrated a previous hypersensitivity reaction to metronidazole, whether orally or topically administered, or any form of parabens.
6. Subjects with primary or secondary immunodeficiency.
7. Women who would have been under treatment during the study period for cervical intra-epithelial neoplasia (CIN) or cervical carcinoma.
8. Subjects who were pregnant, breast feeding, or planning a pregnancy.
9. Subjects who were menstruating at the time of diagnosis.
10. Subjects with intrauterine devices.
11. Concurrent anticoagulation therapy with comadin or warfarin.
12. Concurrent use of systemic corticosteroids or systemic antibiotics.
13. Subjects with clinically significant unstable medical disorders, life threatening diseases, or current malignancies.
14. Subjects previously enrolled in this study.
15. Subjects who had participated in another clinical trial or had taken an experimental drug within the past 30 days.
16. Subjects who were unwilling or unable to comply with the requirements of the protocol.

Three subject populations were defined: intent-to-treat (ITT), modified intent-to-treat (mITT), and per-protocol (PP). An ITT subject was any individual who received study medication and returned for at least one follow-up visit. A mITT subject was any individual who (a) met all inclusion/exclusion criteria, (b) received study medication, (c) returned for at least one follow-up visit, and (d) had a negative test result for *Neisseria gonorrhoeae, Chlamydia trachomatis*, and a Gram's stain slide Nugent Score≧4 at Visit 1. A PP subject was any individual who (a) met all inclusion/exclusion criteria, (b) was compliant with study medication (received at least 3 consecutive days of therapy and no more than 6 days of therapy), (c) had no study violations which could have altered the effect of, or the accurate assessment of, the applied study treatment, and (d) was assessed for efficacy at Visit 3 (within Day 22 to Day 31) or defined as failure at Visit 2. Safety analyses were conducted on the ITT population, and efficacy analyses were conducted on both the PP and the mITT populations.

Five hundred seventy-nine (579) subjects were enrolled into the study, were randomized to either one of the two treatment groups, and received treatment. Two hundred ninety-three (293) subjects received the Test Product and two hundred eighty-six (286) subjects received the Reference Product. One hundred twenty (120) subjects failed to use study medication and/or failed to return for at least one follow-up visit, and were therefore excluded from the ITT analysis; the remaining 459 subjects were included in the ITT analyses. Four hundred twenty-one (421) subjects were included in the mITT analyses and three hundred fourteen (314) subjects were included in the PP analyses.

The primary efficacy endpoint was the therapeutic cure rate, which included both the clinical response and the Nugent Score, of the subject at the Test-of-Cure Visit (Visit 3). The secondary efficacy endpoint was the therapeutic cure rate at the Post-treatment Visit (Visit 2).

A therapeutic cure was defined as a subject who was considered both a clinical cure and a bacterialogical cure (Nugent score of 0-3). A clinical cure was defined as resolution of the clinical findings from the baseline visit. Subjects had all of the following:
   The original discharge characteristic of bacterial vaginosis had returned to a normal physiological discharge, which varies in appearance and consistency depending on the menstrual cycle.
   The 10% KOH "whiff test" was negative.
   The saline wet mount was negative for clue cells.
   The vaginal fluid pH was <4.7.

A clinical failure was defined as a subject who did not meet the definition of clinical cure, or the investigator felt that the subject required additional treatment for bacterial vaginosis infection.

A two-sided 90% confidence interval about the difference in therapeutic cure rates between the test and reference products was constructed by Wald's method with Yates' continuity correction based on the data of PP subjects pooled from all clinical centers. (See, e.g., John J. Hickey, "Sampling Economy and Process Capability Decisions" available at http://www.isixsigma.com/library/content/c030811a.asp; http://en.wikipedia.org/wiki/Yates'_correction_for_continuity.)

Bioequivalence of the test product to the reference product was obtained if the confidence bounds of the 90% confidence interval were contained within the limits −0.20 (−20%) to 0.20 (20%). No formal statistical analyses were performed to detect treatment-by-center interactions. Analysis results were summarized by center, and the homogeneity of treatment effects was investigated using descriptive statistics. If a significant treatment-by-center interaction was observed the nature and effect of this interaction was examined. A significant effect was defined as a difference in test-to-reference success proportions within a center that was opposite in sign and whose magnitude exceeded the mean difference across all centers by at least three-fold.

The above analyses were also conducted on the mITT population to evaluate the consistency of the PP subject findings.

Treatment and Results

A vaginal gel containing 0.75 weight percent metronidazole was prepared according to the procedure of Example 1. One applicator-full of the gel (about 5 grams) was self-administered once a day, at bedtime, for five consecutive days. Thus, each unit dose contained about 37.5 mg of metronidazole, and the total dose was about 187.5 mg. A subject was considered to be "per protocol" if she received at least three consecutive days of therapy, but not more than six total days of therapy, as determined from a diary card.

Each patient was examined twice after beginning treatment on day 1, once between days 8 and 15, and again between days 22 and 31. At the Investigator's discretion, an unscheduled visit may have been performed. If the subject was discontinued during this visit, the End of Study CRF was completed. Adverse events and any changes in concomitant medications was recorded. A pelvic exam was performed and specimens were collected for the following tests:

Saline "wet mount" to check for the presence of clue cells and *Trichomonas vaginalis*
10% KOH "whiff test"
Vaginal fluid pH
Gram's stain (The slide was sent to the central reference lab for Nugent scoring. See, e.g., Nugent et al., "Reliability of Diagnosing Bacterial Vaginosis is Improved by a Standardized Method of Gram Stain Interpretation," J. Clin. Microbiol, 29: 297-301 (1991).)
Urine pregnancy
*Chlamydia trachomatis* LCx assay (if clinically necessary)
*Neisseria gonorrhoeae* LCx assay (if clinically necessary)

A completed subject is a subject who satisfied all study entry criteria, completed the 5-day double-blind treatment phase, and returned for all required visits.

Study protocol violations were defined as any subject or investigator activity which could have altered the effect of, or the accurate assessment of, the applied study treatment. Subjects with protocol violations were excluded from the PP analyses. These study protocol violations included the following:

Failure to return for at least one follow-up visit
Had a positive test result for *Neisseria gonorrhoeae* or *Chlamydia trachomatis*, or a Gram's stain slide Nugent Score≧4 at Visit 1
Violation of inclusion or exclusion criteria
Was missing an efficacy assessment at Visit 3 unless defined as failure at Visit 2
Received less than 3 consecutive days of therapy or more than 6 days of therapy
Began study treatment more than 2 days after the Baseline visit
Had a study violation which could have altered the effect of, or the accurate assessment of, the applied study treatment (such as using an intravaginal product or a prohibited medication)

Study protocol deviations were defined as various from the protocol that did not alter the effect of, or the accurate assessment of, the applied study treatment, and therefore did not preclude inclusion in the PP analyses. Subjects with protocol deviations were included in the PP analyses. These study protocol deviations included the following:

Presence of vaginal discharge unrelated to bacterial vaginosis
Menses during a study visit
pH≧4.7 unrelated to bacterial vaginosis
Use of intravaginal products post-treatment
Use of certain concomitant medications
Removal of shrinkwrap on medication tube Safety and Tolerance Of the 459 ITT subjects, 209 experienced one or more treatment-emergent adverse events (AEs) during the study. The percent of subjects with AEs regardless of relationship to study medication was 41.8% in the test group and 49.0% in the reference group. The percent of subjects with AEs probably or definitely related to study medication was 11.4% in the test group and 17.2% in the reference group. The two treatment groups were comparable. There was no significant statistical difference between the two treatment groups with regard to AE occurrence, severity, or relationship to treatment (p>0.05). In sum, the study did not demonstrate any safety concerns for adults with bacterial vaginosis.

Efficacy

The efficacy results of the study are shown in Table II, below.

TABLE II

| Efficacy Endpoint | Subjects | Example 1 (0.75%) | MetroGel-Vaginal ® (0.75%) | 90% Confidence Interval |
|---|---|---|---|---|
| Primary Efficacy: Therapeutic Cure Rate At Visit 3 | Per-Protocol (PP) | 86 (55%) (N = 155) | 63 (40%) (N = 159) | (6.07%, 25.65%) |
| | Modified Intent-To-Treat* (mITT) | 111 (54%) (N = 206) | 89 (41%) (N = 215) | (4.07%, 20.91%) |

TABLE II-continued

| Efficacy Endpoint | Subjects | Example 1 (0.75%) | MetroGel-Vaginal ® (0.75%) | 90% Confidence Interval |
| --- | --- | --- | --- | --- |
| Secondary Efficacy: Therapeutic Cure Rate At Visit 2 | Per-Protocol (PP) | 100 (65%) (N = 155) | 78 (49%) (N = 159) | (5.67%, 25.46%) |
| | Modified Intent-To-Treat* (mITT) | 134 (65%) (N = 206) | 113 (53%) (N = 215) | (4.19%, 20.79%) |

*A last-observation-carried-forward (LOCF) approach was used for missing efficacy results for the mITT subjects.

According to this clinical study, the formulation of Example 1 was not bioequivalent to MetroGel-Vaginal® using a 90% confidence interval about the difference in therapeutic cure rate. The formulation of Example 1 produced a superior therapeutic cure rate.

What is claimed is:

1. A viscous vaginal pharmaceutical composition comprising an aqueous gel consisting essentially of:
    about 0.75% metronidazole;
    about 3.5% hypromellose;
    about 3% propylene glycol;
    about 0.05% edetate disodium; and
    about 0.08% methylparaben;
    about 0.02% propylparaben; and
    about 93% water,
    wherein the pH of the composition is from about 5 to about 6.5.

2. A vaginal insert comprising the composition of claim 1 housed in a medical device having a means for controlling the dose of the active pharmaceutical ingredient to a patient.

\* \* \* \* \*